United States Patent
Weiss et al.

(10) Patent No.: US 7,247,463 B2
(45) Date of Patent: Jul. 24, 2007

(54) ENZYMES WITH LIPASE/ACYLTRANSFERASE ACTIVITY, NUCLEIC ACIDS ENCODING THE SAME AND METHODS OF USE THEREOF

(75) Inventors: Albrecht Weiss, Langenfeld (DE); Frederic Bigey, Montpellier (FR); Eric Dubreucq, Montpellier (FR); Guy Moulin, Montferrier-sur-Lez (FR)

(73) Assignee: Cognis Deutschland GmbH & Co. KG, Duesseldorf (DE)

( * ) Notice: Subject to any disclaimer, the term of this patent is extended or adjusted under 35 U.S.C. 154(b) by 451 days.

(21) Appl. No.: 10/681,636

(22) Filed: Oct. 8, 2003

(65) Prior Publication Data

US 2004/0142441 A1 Jul. 22, 2004

Related U.S. Application Data

(60) Provisional application No. 60/416,987, filed on Oct. 8, 2002.

(51) Int. Cl.
C12N 9/10 (2006.01)
C12N 9/20 (2006.01)
(52) U.S. Cl. ....................... 435/193; 435/198; 536/23.2
(58) Field of Classification Search ................. 435/193, 435/198; 536/23.2
See application file for complete search history.

(56) References Cited

FOREIGN PATENT DOCUMENTS

DE 197 53 789 A1 6/1999

OTHER PUBLICATIONS

Sequence search alignment between SEQ ID No. 2 and accession No. Q8NIN8.*
Lipman, D.J., et al., "Rapid and Sensitive Protein Similarity Searches", Science, 227:1435-1441, (1985).
Kouker, G., et al., "Specific and Sensitive Plate Assay for Bacterial Lipases", Applied and Environmental Microbiology, 53:211-213 (1987).
Vaysse, L., et al., "Fatty hydroxamic acid biosynthesis in aqeous medium in the presence of the lipase-acyltransferase from Candida parapsilosis", J. of Biotechnology, 53:41-46 (1997).
EMBL database, entry name: Z9P8W1, Gene name: LIP4, accessed Dec. 13, 2001.
EMBL database, gene: LIP1, accessed Dec. 13, 2001.
Fu, Y., et al., "Cloning and characterization of a gene (LIP1) which encodes a lipase from the pathogenic yeast Candida albicans", Microbiology 143:331-340 (1997).
EMBL database, entry name: O94015, gene name: CA35A5.09, accessed Dec. 13, 2001.
Tait, E., et al., "A Candida albicans Genome Project: Cosmid Contigs, Physical Mapping, and Gene Isolation", Fungal Genetics and Biology, 21:308-314 (1997).
Definitions from "Lexikon der Biochemie" for DNA Synthese; Spektrum Akademischer Verlag, Berlin, 1999, vol. 1 p. 267-271 and vol. 2, p. 227-229.
Hube, B., et al., "Secreted lipases of Candida albicans: cloning, characterization and expression analysis of a new gene family with at least ten members", Arch. Microbiol., 174: 362-374 (2000).
Bradford, M.M., "A Rapid and Sensitive Method for Quantitation of Microgram Quantities of Protein Utilizing the Principle of Protein-Dye Binding", Analytical Biochemistry 72:248-254 (1976).
Bigey, F., et al., " Identification of a triaclyglycerol lipase gene family in Candida deformans: molecular cloning and functional expression", Yeast, 20(3):233-48 (2003).
Abstract in PubMed—Howard, G.T., et al., "Sensitive plate assay for screening and detection of bacterial polyurethanase activity", Lett. Appl. Microbiol., 32(3):211-4 (2001).
Abstract in PubMed—Li, X., et al., "Gene cloning, sequence analysis, purification, and secretion by Escherichia coli of an extracellular lipase from Serratia marcescens", Appl. Environ. Microbiol. 61(7):2674-80 (1995).
Jette, J.F., et al., "Determination of Lipase Activity by a Rhodamine-Triglyceride-Agarose Assay", Analytical Biochemistry, 219:256-260 (1994).
Briand, D., et al., "Substrate Specificity of the Lipase from Candida parapsilosis", Lipids, 30:747-754 (1995).
Briand, D., et al., "Enzymatic Fatty Esters Synthesis In Aqueous Medium With Lipase From Candida parapsilosis (Ashford) Langeron And Talice", Biotechnology Letters 16:813-818 (1994).
Neugnot, V., et al., "The lipase/acyltransferase from Candida parapsilosis: Molecular cloning and characterization of purified recombinant enzymes", Eur. J. Biochem., 269:1734-1745 (2002).
Abstract Briand, D., et al., "Functioning and regioselectivity of the lipase of Candida-parapsilosis (Ashford) langeron and talice in aqueous-medium—New interpretation of regioselectivity taking acyl migration into account", European Journal of Biochemistry, 228:169-175 (1995).
Fournand, D., et al., "Monohydroxamic acid biosynthesis", Journal of Molecular Catalysis B: Enzymatic 5: 207-211 (1998).
Boze, H., et al., "High-level secretory production of recombinant porcine follicle-stimulating hormone by Pichia pastoris", Process Biochemistry, 36:907-913, (2001).

* cited by examiner

*Primary Examiner*—Tekchand Saidha
(74) *Attorney, Agent, or Firm*—John F. Daniels

(57) ABSTRACT

Polypeptides with lipase/acyltransferase activity are described with an amino acid sequence which has identity to the sequence reported in SEQ ID NO 2 of at least 49%, also polypeptides which display this activity, as well as nucleic acids (genes) which code for these polypeptides, vectors which contain nucleic acids which code for these polypeptides, transformed microorganisms which contain these nucleic acids, processes for production of these polypeptides and the application of nucleic acids for discovering new lipase/acyltransferases and the use of these lipase/acyltransferases as catalysts in chemical and biochemical processes.

13 Claims, 3 Drawing Sheets

Figure 1: Vector pVT100CpLIP2
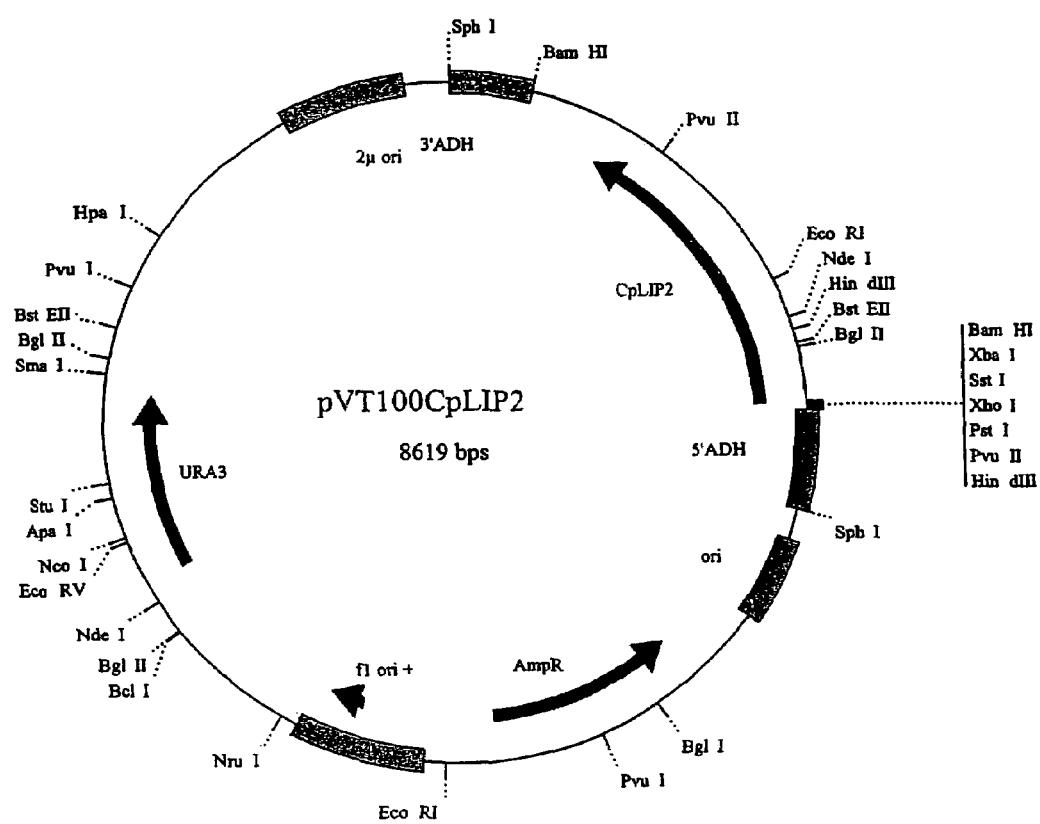

Figure 2: Vector pPIC9KCpLIP2
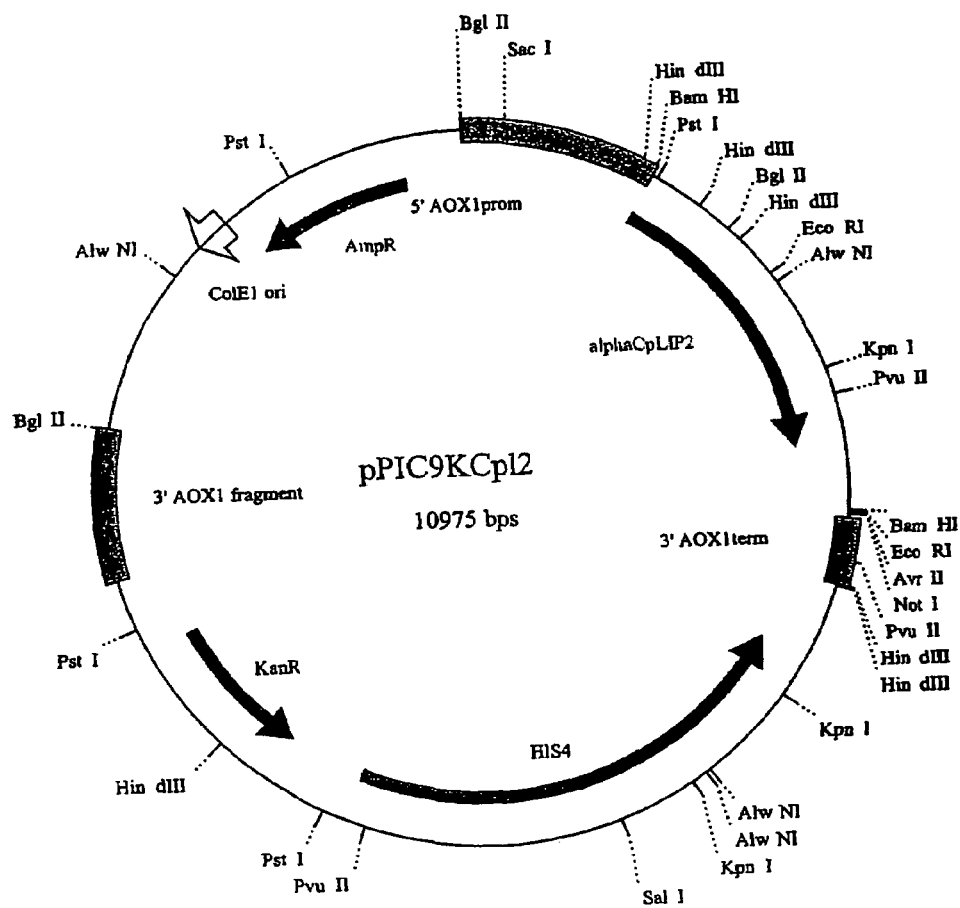

Figure 3: Vector pVT100CpLIP2His
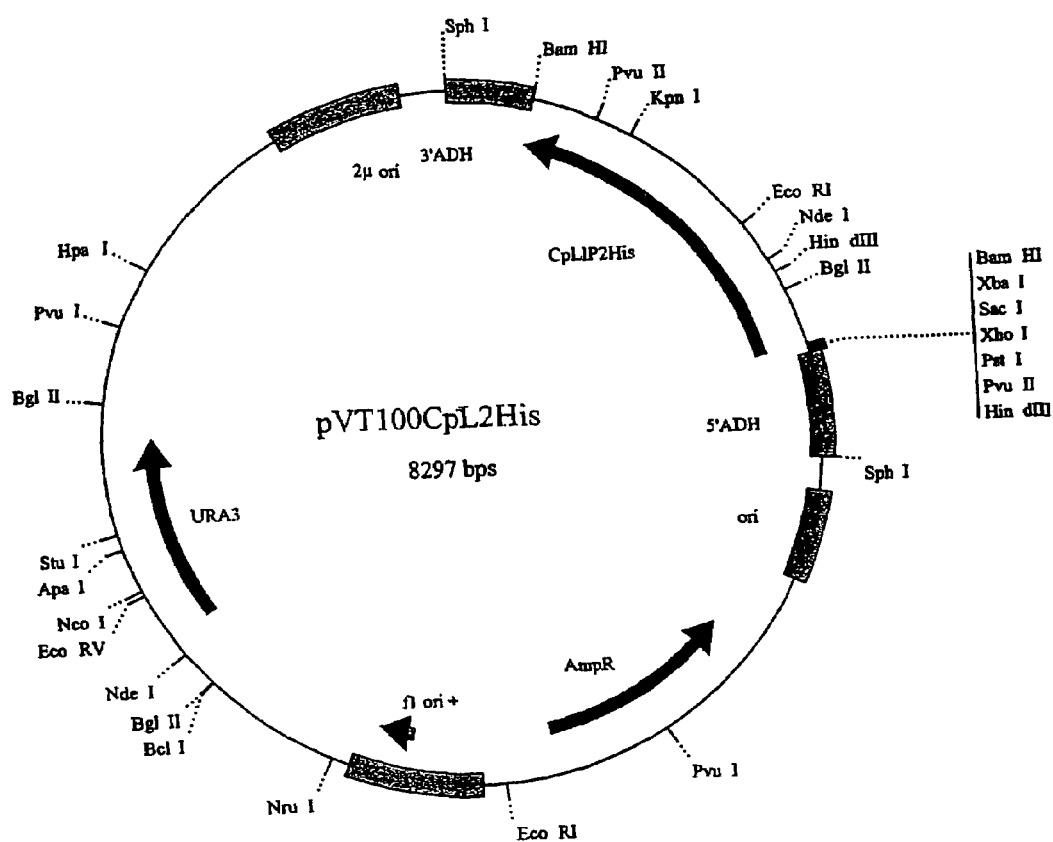

US 7,247,463 B2

ENZYMES WITH LIPASE/ACYLTRANSFERASE ACTIVITY, NUCLEIC ACIDS ENCODING THE SAME AND METHODS OF USE THEREOF

CROSS REFERENCE TO RELATED APPLICATION

This application claims priority to U.S. Provisional Application No. 60/416,987 filed Oct. 8, 2002, the entire disclosure of which is incorporated by reference herein.

FIELD OF THE INVENTION

The present invention relates to nucleic acid sequences encoding lipase/acyltransferases and functional fragments thereof. Also provided are methods of use of such lipases as catalysts in chemical and biochemical processes.

BACKGROUND OF THE INVENTION

Several references and patents are cited throughout the present application in order to more clearly describe the state of the art to which the invention pertains. Each of the above described citations is incorporated by reference herein.

In conventional (non-enzymatic) chemical synthesis processes, esterification of compounds with multiple hydroxyl groups (e.g., polyalcohols such as glycerol), will, in general, yield a product mixture of mono- and poly-substituted esters, rather than a product with predominantly only one particular hydroxyl group esterified. The esterification can be made selective by adding protecting groups prior to the esterification step. The protecting groups are then normally removed after the esterification. The use of such protecting groups complicates and adds expense to the synthesis. Similarly, synthesis routes involving activated carboxylic acid derivatives form undesired secondary products. The formation of unwanted secondary products reduces the yield of the desired products, burdens subsequent purification steps, and may create additional waste disposal issues.

Another class of reactions prevalent in the processing of fats include transesterifications, re-esterifications, and acyl-transfers. Enzymatic processes for esterification or reesterification and acyltransfer are well known in the art. For instance,it is well established that transesterification can be catalyzed by lipases in water-free media. If water is present in the reaction of esters, alcohol and lipases, cleavage of the acids and/or intermediates thereof normally occurs. Since various lipases also catalyze the formation of esters from free fatty acids and alcohols, lipase catalyzed transesterifications normally proceed through an acid intermediate stage. However, in many commercial processes, the presence of free acids is undesirable. The water content prevents, to some extent, a technically and commercially acceptable reaction (formation of an unfavorable thermodynamic equilibrium). Thus, costly operations including water removal by such methods as azeotropic distillation, membrane separation processes, vacuum distillation have been employed in order to achieve satisfactory yields.

The above mentioned difficulties can be avoided, or at least partly ameliorated, by employing enzyme catalysts. The use of enzyme catalysts 1) permits milder reaction conditions, 2) enhances the selectivity of the synthesis, 3) reduces unwanted secondary products, 4) results in a less expensive synthetic process and 5) facilitates post-synthesis purification.

In light of the above, enzyme catalysis is finding increasing and wider application in chemical and biochemical synthesis. More specifically, and more germane to the present invention, hydrolases and especially lipases (two classes of proteins with enzyme activity for breaking down molecules) are employed for splitting fat compounds (e.g., triacyl glycerides) in large-scale industrial processes. It is an object of the invention to provide improved lipases/acyltransferases and nucleic acids encoding the same, for this and a variety of other purposes.

SUMMARY OF THE INVENTION

In accordance with the present invention, methods and compositions for catalyzing lipolysis and other enzymatic reactions used in the processing of fats are provided. One embodiment of the invention comprises a nucleic acid encoding a lipase/acyltransferase of SEQ ID NO: 2. An exemplary nucleic acid for this purpose comprises SEQ ID NO: 1. Also provided is SEQ ID NO: 3 which encodes a lipase/acyltransferase protein operably linked to a histidine tag. This polypeptide has the amino acid sequence of SEQ ID NO: 4. Also provide are derivatives and variants of the aforementioned sequences, e.g., deletion, insertion and chemically modified sequences. In a further aspect of the invention, vectors containing the above-described nucleic acids are disclosed. The invention also encompasses host cells comprising a vector encoding a lipase/acyltransferase for production of the same.

In another aspect of the invention, an antibody (Ab) specific for the lipase/acyltransferase is provided. Such antibodies may be monoclonal, polyclonal or antigen binding fragments. Immunospecific antibodies of the present invention have utility in the isolation of polypeptide homologues of the presently disclosed lipase/acyltransferase.

Methods for detecting homologous lipase/acyltransferase encoding nucleic acids in biological samples are also disclosed. Exemplary methods include, without limitation, in situ hybridization, polymerase chain reaction, Southern and Northern Blotting. Such methods also encompass the propagation and isolation of microorganisms encoding these homologues followed by cloning and sequencing of the homologous lipase/acyltransferase sequences.

In a further aspect, methods for employing a lipase/acyltransferase of the invention in a variety of lipolysis reactions are disclosed.

Accordingly, an object of the present invention is to produce and utilize polypeptides and proteins that will catalyze acyl transfer reactions in high yields, even in media with relatively high water content, thereby circumventing a major disadvantage associated with conventional lipase-catalyzed esterification. The availability of sequence information for the relevant nucleic acids facilitates modifications to the sequence which optimize the expression, secretion, purification, enzyme activity, and other properties of lipase/acyltransferase enzymes, including their stability, immunogenic activity, and working range of activity with respect to temperature, pH, ionic strength, etc. Such modifications can be effected by, for example, site-directed mutagenesis, truncation, fusion, and domain shuffling.

The following definitions are provided to facilitate an understanding of the present invention.

The term "polypeptide" refers to a polymer composed of amino acids. In the present application, the 19 naturally occurring L-amino acids and glycine are designated by the conventional 1 and 3 letter codes. Another more limiting designation for a polypeptide is the term protein, in which case the number of amino acid residues in the polypeptide is greater than 50.

The term "lipase/acyltransferase activity" refers to the activity of a polypeptide or enzyme which combines the properties of lipases with the properties of acyltransferases. Lipases belong to the group of hydrolases (especially the esterases) which split specific fats (triglycerides) into glycerin (sometimes referred to as glycerol) and fatty acids. This process, called lipolysis, —normally occurs at the phase boundary between a hydrophobic phase containing the fat and a hydrophilic aqueous phase. Acyltransferases are also designated as transacylases—and can be included in the enzyme classification known as transferases. Quite generally, acyl transferases transfer acyl or especially acetyl groups from a donor molecule to an acceptor molecule, and for this reason, are of particular importance in the synthesis and breakdown of fats. Studies of the lipase/acyltransferase which is the subject of the present invention have shown that this polypeptide is functional at the water-lipid phase boundary and catalyzes a reaction which is characteristic for lipases. It has also been found that this polypeptide is capable of catalyzing transesterifications at a water content in the reaction mixture corresponding to a water activity greater than 0.8. At this high a level of water, other lipases would typically catalyze only the hydrolysis of esters. Therefore, the polypeptides according to the invention exhibit characteristics of both lipases and acyltransferases. Based on its sequence homology with previously established lipases isolated from *Candida albicans*, the polypeptide of the present invention is referred to as lipase. At the same time, on the basis of its enzyme activity, the peptide of the present invention can be considered an acyltransferase.

The preferred donor substrates in reactions catalyzed by the lipase/acyltransferase of the invention include all possible esters, such as fats, and more specifically, triglycerides, 1,3-diglycerides, 1,2 diglycerides, and 1-monoglycerides. The preferred acceptor molecules in reactions catalyzed by the lipase/acyltransferase of the invention include primary and secondary alcohols with 1 to 5 carbon atoms, especially ethanol, propanol, butanol, 1,2-propaneiol propanediol, 1,3-propane diol, 2-methyl-1-propanol, 2-methyl- 1-butanol, 3-methyl-1 butabol, and various hydroxylamines.

The term "identity" when used with respect to an amino acid sequence designates a 5 homology, i.e., a sequence similarity in that many of the amino acids at equivalent positions in the two sequences being compared are the same. Homologies and sequence similarities can be quantified. A 100% homology indicates complete identity, i.e., both polypeptides have the same sequence. Percentages less than 100% indicate that some amino acids at equivalent positions differ, and further, the lower the percentage, the greater the number of of divergent amino acids at a given position. In general, two polypeptides with a high degree of homology can be expected to have similar chemical and/or biological function and activity. The identity of a nucleotide sequence pertains to a gene or protein coding sequence that is homologous to a reference nucleotide sequence. Here, the term homologous is construed to mean that the gene or coding sequence may be allelic. Homologous can also be construed to mean that the gene may originate from another species and that the polypeptide coded by this gene has the same biological activity as the polypeptide coded by the reference nucleotide sequence. Polypeptides having lipase/acyltransferase activity whose amino acid sequence is identical to 49%, to 80% to 96%, to 96.5%, to 97%, to 97.5% to 98%, to 98.5% to 99% to 99.5%, to 99.8% or to 100% to the amino acids sequence reported in SEQ ID NO: 2 are encompassed in the present invention. This is especially true for those partial regions of the protein which involve amino acids 190-390. A polypeptide which possesses 100% identity to the amino acids sequence reported in SEQ ID NO: 2 contains 465 amino acids. A 96% identity is especially preferred for the partial regions in positions 190-200, 220-290 and 330-385, especially for positions 196, 240 and 381. Variants of SEQ ID NO: 1 which encode a functional lipase/acyltransferase are also within the scope of the invention. Nucleic acids encoding a polypeptide having lipase/acyltransferase activity whose nucleic acid sequence is identical to 49%, to 80% to 96%, to 96.5%, to 97%, to 97.5% to 98%, to 98.5% to 99% to 99.5%, to 99.8% or to 100% to the nucleic acids sequence reported in SEQ ID NO: 1 are also encompassed in the present invention.

The term "fragment" refers to polypeptides that are smaller than the naturally-occuring proteins to which they are related, and/or from which they originate. They may be related to a corresponding naturally-occuring, and generally larger, protein based on similarities in their amino acid sequence. Fragments may also be related to a corresponding protein based on similarities in secondary and tertiary structure, or similarities in function or behavior such as binding to or complexing of substrates, catalytic activity, or immunogenic response. Fragments generally represent truncated versions of naturally-occuring proteins, either by removal of sequences from the carboxy-terminal and/or amino-terminal ends of the protein, or by removal of domains, i.e., parts of a protein that fold independently or have distinct function, from a naturally-occuring protein. Such fragments may be more cheaply produced, may no longer possess possibly unfavorable characteristics of the original molecule such as possibly an activity-lowering regulation mechanism or manifest a more favorable activity profile. Such protein fragments may also be synthesized both biosynthetically or chemically. Chemical synthesis may be advantageous, for example, whenever chemical modifications are to be undertaken following the synthesis.

It is sometimes useful to distinguish fragments from proteins that differ only from their corresponding naturally occurring proteins by deletion or insertion of a small number of amino acids.

In the sense of the present invention, the term chimeric or hybrid polypeptide, refers to those proteins which are composed of amino acid sequences from different and distinct proteins derived either from the same or different organisms. Chimeric or hybrid proteins can be made by shuffling or fusion mutagenesis. This is best accomplished at the nucleic acid level by ligating nucleic acid sequences that code for different proteins into a single nucleic acid or gene product. Such a fusion protein may, for example, show enhanced activity or a combination of activities or properties not found in the component polypeptides from which the fused protein is constructed. It is of no consequence whether such a chimeric protein consists of an individual polypeptide chain or several subunits among which different functions may be distributed. To realize the last-mentioned alternative, for example, selective proteolytic splitting can be used to cleave a single chimeric polypeptide chain into several.

The term 'polypeptide obtained by insertion mutation' refers to those polypeptides that are obtained by known methods wherein a nucleotide or several nucleotides are inserted into specific sites of the nucleic acid sequence of interest. Inversion mutagenesis, encompassing a partial sequence reversal, can be regarded as a special form of modification which includes deletion and insertion.

The term 'peptide derivatives' signifies polypeptides in which some of the amino acid side chains of the polypeptide have been chemically modified. Such derivatizations, termed post-translational modifications, occur naturally in eukayotic organisms and include glycosylation with sugar moieties and acylation with fatty acids. Post-translational modifications are not random, but are targeted to specific amino acids of the peptide that are part of short sequences that promote enzymatic modification of amino acid side chains. The nature and degree of post-translational modification is specific to the particular organism in which the protein is expressed.

Peptides can also be derivatized by ex vivo chemical transformation of a side chain of an amino acid or by covalent bonding of another compound to the protein. Such a compound, for example, may involve other proteins, which, for example, are bound via bifunctional chemical compounds to the polypeptide according to the invention. The term 'derivatization' also refers to covalent binding to a macromolecular carrier. Such modifications may, for example, influence the substrate specificity or the bond strength to the substrate or bring about a modification of the enzymatic activity if the substance linked to the polypeptide acts as an inhibitor. Such a reversible inactivation of the enzyme may be convenient for handling and storage of the enzyme. A more specific example of such post-translational modifications are derivatives that are obtained by covalent binding to a macromolecular carrier such as polyethylene glycol or a polysaccharide.

Deoxyribose nucleic acids (DNA), and the implicit protein sequences encoded therein, are stable repositories of genetic information, and are preferred over ribonucleic acid (RNA; a transient carrier of genetic information that is prone to degradation) for manipulating and processing by various biochemical and biotechnology techniques. However, it will be understood that all of the deoxyribose nucleic acid sequences described herein, will imply a corresponding ribonucleic acid (RNA) sequence, and methods based utilizing ribonucleic acids such as Northern blotting In the case of DNA, the sequences of the two complementary strands are to be considered in each case in all three possible reading grids. It is also noted that different codon triplets may code for the same amino acids so that a specific amino acid sequence may be derived from several different possibly only slightly identical nucleotide sequences (degenerateness of the genetic code or "wobble codon"). In addition different organisms display differences in the use of these codons. For these reasons both amino acid sequences as well as nucleotide sequences are included in the scope of the present invention, and the reported nucleotide sequences in each case are to be regarded only as examples of coding for a specific amino acid sequence.

The phrase "consisting essentially of" when referring to a particular nucleotide or amino acid means a sequence having the properties of a given SEQ ID No:. For example, when used in reference to an amino acid sequence, the phrase includes the sequence per se and molecular modifications that would not affect the basic and novel characteristics of the sequence.

In accordance with the present invention, nucleic acids having the appropriate sequence homology with the nucleic acids of the invention may be identified by using hybridization and washing conditions of appropriate stringency. For example, hybridizations may be performed, according to the method of Sambrook et al. (1989, *Molecular Cloning*, Cold Spring Harbor Laboratory), using a hybridization solution comprising: 5×SSC, 5×Denhardt's reagent, 1.0% SDS, 100 µg/ml denatured, fragmented salmon sperm DNA, 0.05% sodium pyrophosphate and up to 50% formamide. Hybridization is carried out at 37-42° C. for at least six hours. Following hybridization, filters are washed as follows: (1) 5 minutes at room temperature in 2×SSC and 1% SDS ; (2) 15 minutes at room temperature in 2×SSC and 0.1% SDS; (3) 30 minutes-1 hour at 37° C. in 1×SSC and 1% SDS; (4) 2 hours at 42-65° C. in 1×SSC and 1% SDS, changing the solution every 30 minutes.

One common formula for calculating the stringency conditions required to achieve hybridization between nucleic acid molecules of a specified sequence homology (Sambrook et al., 1989, supra):

$$T_m=81.5° C.+16.6 \text{ Log } [Na+]+0.41(\% \text{ G+C})-0.63(\% \text{ formamide})-600/\#bp \text{ in duplex}$$

As an illustration of the above formula, using [Na+]= 0.368 and 50% formamide, with GC content of 42% and an average probe size of 200 bases, the $T_m$ is 57° C. The $T_m$ of a DNA duplex decreases by 1-1.5° C. with every 1% decrease in homology. Thus, targets with greater than about 75% sequence identity would be observed using a hybridization temperature of 42° C.

The stringency of the hybridization and wash depend primarily on the salt concentration and temperature of the solutions. In general, to maximize the rate of annealing of the probe with its target, the hybridization is usually carried out at salt and temperature conditions that are 20-25° C. below the calculated $T_m$ of the hybrid. Wash conditions should be as stringent as possible for the degree of identity of the probe for the target. In general, wash conditions are selected to be approximately 12-20° C. below the $T_m$ of the hybrid. In regards to the nucleic acids of the current invention, a moderate stringency hybridization is defined as hybridization in 6×SSC, 5×Denhardt's solution, 0.5% SDS and 100 µg/ml denatured salmon sperm DNA at 42° C., and washed in 2×SSC and 0.5% SDS at 55° C. for 15 minutes. A high stringency hybridization is defined as hybridization in 6×SSC, 5×Denhardt's solution, 0.5% SDS and 100 µg/ml denatured salmon sperm DNA at 42° C., and washed in 1×SSC and 0.5% SDS at 65° C. for 15 minutes. A very high stringency hybridization is defined as hybridization in 6×SSC, 5×Denhardt's solution, 0.5% SDS and 100 µg/ml denatured salmon sperm DNA at 42° C., and washed in 0.1×SSC and 0.5% SDS at 65° C. for 15 minutes.

The information unit corresponding to a protein is also designated as a gene in the sense of the present invention.

Nucleic acid sequence information can be used to construct various primers for the polymerase chain reaction. The polymerase change reaction can be used for amplifying the amount of nucleic acids, site-directed mutagenesis of nucleic acid sequences, and for creating gene fusions that sequentially combine sequences from distinct genes. Further, polymerase chain reaction techniques permit the inclusion of tag sequences that facilitate isolation and separation of proteins encoded by the sequence.

Changes in the nucleotide sequence such as may be caused for example, by known molecular-biological methods, are called mutations. Types of mutations include deletion, insertion or substitution mutations or those in which different genes or parts of genes are fused to each other (shuffling); these are gene mutations. The corresponding organisms are called mutants. The proteins derived from mutated nucleic acids are designated as variants. Thus, for example, deletion, insertion, substitution mutations or fusions lead to deletion, insertion, or substitution-mutated or fusion genes and on the protein level to the corresponding deletion, insertion or substitution variants or fusion proteins respectively.

BRIEF DESCRIPTION OF THE DRAWINGS

FIG. 1 is a restriction map of the vector pVT100CpLIP2.
FIG. 2 is a restriction map of the replicative vector pPIC9KCpLIP2.
FIG. 3 is a restriction map of the integrative vector pVT100CpLIP2His.

DETAILED DESCRIPTION OF THE INVENTION

A unique polypeptide isolated from the microorganism *Candida parapsilosis* CBS 604 is provided which displays lipase/acyltransferase activity. The enzymatic activity of this polypeptide has been studied in transesterification reactions. It is possible to maintain nearly acid-free conditions even in the presence of water at concentrations as high as 80 mole percent. Accordingly, use of the enzyme of the present invention obviates the need for costly water removal steps.

An exemplary nucleic acid encoding the lipase/acyltransferase of the invention comprises SEQ ID NO:1. The polypeptide encoded by SEQ ID NO: 1 has the amino acid sequence of SEQ ID NO: 2 and a molecular weight of between 49 and 55kD after deglycosylation, most preferably 54 kD. The nucleic acid of SEQ ID NO. 1 and polypeptides resulting from expression of this nucleic acid, and the polypeptide of SEQ ID NO:2 can be manipulated and modified by established methods of biotechnology. The present invention specifies and teaches means by which the nucleic acid of SEQ ID NO: 1 and nucleic acids related to, or derived from, the nucleic acid of SEQ ID NO: 1, and the polypeptide sequence of SEQ ID NO:2, and polypeptides related to, or derived from, the polypeptide of SEQ ID NO: 2, can be used to produce enzymes with lipase/acytransferase activity, and especially enzymes with unique attributes compared to other lipases.

Also encompassed with in the invention are polypeptides with lipase/acyltransferase activity with an amino acid sequence which possesses homology to the amino acid sequence reported in SEQ ID NO:2 of at least 49%, preferably 80%, more preferably at least 98%, still more preferably 99.8% and most preferably 100%. As a more particular specification, a polypeptide with an amino acid sequence with 96% identity to the sequence ranging from residues 190 to 390 of the polypeptide identified by SEQ ID NO: is a subject of the present invention.

The nucleic acids of the present invention, or parts of the nucleic acids of the present invention, may be used as probes in screening genomes, such as in Southern blotting techniques, or as primers for the polymerase chain reaction.

The present invention also provides a variety of cloning/expression vectors for the production of variants of the peptides specified above in several host microorganisms including several strains of yeast. Another aspect of the invention is the use of nucleic acid probes to isolate naturally-occuring strains of microorganisms that produce the enzymes that are a subject of the invention. Still another aspect of the invention is the production of antibodies, produced as part of an immunoresponse in animals challenged with the Polypeptides or proteins that are the subject of the present invention, where said antibodies can be used to screen for strains of naturally-occuring microorganisms that secrete the lipase/acyltransferase enzymes of this invention.

The pH optimum for the catalytic reaction of transesterification, hydrolysis or esterification which was determined at 28° C. is between 3 and 8.5, preferably between 4 and 8, especially between 6 and 7.5.

An optimal temperature range for catalysis of hydrolysis determined at the pH optimum is between 30 and 50° C., preferably between 35 and 40° C. An optimal temperature range for the catalysis of transesterification and esterification determined at the pH optimum is between 20-50° C., preferably between 20 and 30° C.

The polypeptides according to the invention also include those enzymes which display sufficient similarity to them or can be derived by known methods.

In a special variant, the polypeptides with lipase/acyltransferase activity are glycosylated. The positions on which the polypeptide is glycosylated and the degree of glycosylation depend on the organism producing this polypeptide. A degree of glycosylation of 1 to 2 sugar radicals per molecule of polypeptide is preferred.

In another variant of the invention the polypeptides are linked to another peptide. This peptide may involve a marker which, for example, may facilitate purification of the desired polypeptide in subsequent chromatography steps, especially affinity chromatography. A preferred marker for this purpose is a his-tag constructed from 6 monomer histidine units.

Accordingly, also encompassed in the invention are polypeptides with lipase/acyltransferase activity with an amino acid sequence which has identity to the amino acid sequence reported in SEQ ID NO 4 of at least 49%, preferably 80%, preferably at least 98%, especially preferably 99.8% and particularly 100%.

Polypeptide fragments or polypeptides obtained by deletion mutation with a lipase/acyltransferase activity are also within the scope of the invention.

Several variants of the polypeptide with lipase/acyltransferase activity are within the scope of the invention. Such derivatives can be obtained by covalent binding to a macromolecular carrier such as polyethylene glycol or a polysaccharide.

Secondary structural element and its three-dimensional folding of the polypeptide of SEQ ID NO: 2 contribute to enzymatic actitivity. Thus domains deviating clearly from one another in their primary structure in three dimensions may form essentially concordant structures and thus make the same enzymatic behavior possible. Such common features in secondary structure are usually recognized as concordant antigenic determinants of antisera or pure or monoclonal antibodies. Thus similarly structured proteins or derivatives can be detected and classified by immunochemical cross reactions.

Therefore within the scope of the present invention are those polypeptides or derivatives which display lipase/acyltransferase activity and can be assigned to the above-defined proteins or derivatives not so much because of their homology values in the primary structure but rather because of their immunochemical relationships.

Polypeptides according to the invention which stem from natural sources are preferred variants of the present invention, especially if they come from microorganisms such as single celled fungi or bacteria, because the latter can usually be handled much more simply than multicellular organisms or cell cultures derived from multicellular organisms. These represent preferred variants. Especially preferred are polypeptides or derivatives according to the invention from eukaryotic fungi, especially these which can release the secreted proteins directly into the surrounding medium.

Quite especially preferred are polypeptides or derivatives according to the invention which can be obtained from microorganisms selected from the group consisting of *Candida parapsilosis*, and preferably *Candida parapsilosis* CBS 604, *Candida antarctica* (*Trychosporon oryzae*, *Pseudozyma antarctica*), *Candida glabrata*, *Candida albicans*, *Candida maltosa*, *Candida tropicalis*, *Candida viswanathii*, *Issatchenkia orientalis* (*Candida krusei*), *Kluyveromyces marxianus* (*C. kefyr*, *C. pseudotropicalis*), *Pichia guilliermondii* (*Candida guilliermondii*), *Geotrichum candidum*, *Fusarium solani* and *Aeromonas aerophila*.

Among the polypeptides or derivatives from *Candida* species according to the invention, those from *Candida parapsilosis* are preferred. Most preferred are those isolated from *Candida parapsilosis* CBS 604. Isolation of the lipase/acyltransferase of the invention from this species is described in the following examples.

Organisms which naturally form a protein or derivative according to the invention or contain nucleic acids which code for a polypeptide or derivative according to the invention are also within the scope of the invention. Such organisms are obtainable by application of generally well-known techniques, for example, by isolation of strains from a natural habitat, or by screening of gene banks. The nucleotide sequence reported in SEQ ID NO 1 in this case may be used, for example, as a probe for screening, or as a template for construction of corresponding PCR primers.

It is possible that naturally occurring producers may indeed produce an enzyme according to the invention but under the initially defined conditions express it only to a slight degree and/or release it into the surrounding medium only to a minor extent. Nevertheless they fall within the scope of the present invention as long as the possibility exist of finding experimentally suitable environmental conditions or low-molecular weight molecules or other factors that are determined experimentally to stimulate or otherwise enhance production of the protein according to the invention,. Such a regulation mechanism may be used to advantage in biotechnological production. For example, the expression of the protein can be regulated to occur during phases of the micro-organism growth cycle that maximizes protein production and secretion to the surrounding medium.

Depending on the specifics of the recovery, refining, or preparation of a protein it may be associated with various other substances, especially if it is obtained from natural producers of said protein. It may then, but also independently, be mixed selectively with certain other substances, e.g., to increase its storage stability. Therefore, the protein according to the invention that also includes additionally all preparations of the actual protein that are deemed useful for its application in various research, industrial or clinical applications is also a subject of the invention. This is also independent of whether or not it actually manifests this enzymatic activity in a certain preparation, because it may be desirable for it to have no or only low activity during storage and manifest its function only at the time of application. This may, for example, be dependent on the state of folding of the protein or result from the reversible binding of one or more accompanying substances of the preparation or from another control mechanism.

Nucleic acids form the starting point for most molecular biological studies and further developments. Such methods are described, for instance, in the manual by Fritsch, Sambrook and Maniatis, "Molecular cloning: a laboratory manual," Cold Spring Harbour Laboratory Press, NY, 1989. All gene-technical and protein-technical methods known to the state of the art under the heading of protein engineering are based on the gene, especially the cloned gene. With them polypeptides according to the invention can be further optimized with respect to various application, e.g., by point mutagenesis or by fusion with sequences from other genes.

Vectors which contain one of the nucleic acid regions described which code for a polypeptide with lipase/acyltransferase activity for the production of the same are also within the scope of the invention.

In order to deal with nucleic acids the DNA is often cloned in a vector. Vectors are DNA molecules which are suitable transporting molecules (vehicles) for incorporating replicable regulatable, and/or expressable nucleic acids into organisms. Frequently used vectors are plasmids, i.e. extrachromosomal, ring-shaped, double-stranded bacterial DNA which can be introduced by suitable methods into other microorganisms and reproduced there.

The vectors include, e.g., those derived from bacterial plasmids, from viruses or bacteriophages, or predominantly synthetic vectors or plasmids with elements of a variety of origins. With the other genetic elements present in each case, vectors are capable of establishing themselves in the corresponding host cells over several generations as stable units. It is of no import whether they establish themselves extrachromosomally as independent units or are integrated in a chromosome. Which of the numerous systems known from the state of the art is selected depends on the individual case. The selection of a particular vector will depend on the specific application. For instance, the achievable number of copies, the selection systems available, including, above all, antibiotic resistances or the cultivability of the host cells capable of accepting the vectors, will dictate which vector is chosen.

The vectors form suitable starting points for molecular-biological and biochemical studies of the gene in question or of the corresponding protein and for further developments according to the invention and ultimately for amplification and production of proteins according to the invention.

Preferred embodiments of the present invention are cloning vectors. These are suitable, besides for storage, for biological amplification or for selection of the gene of interest, for characterization of the corresponding gene, say by preparation of a restriction map or sequencing. Cloning vectors are also preferred embodiments of the present invention, because they represent a portable and storable form of the claimed DNA. They are also preferred starting points for molecular biological techniques which are not bound to cells such as the polymerase chain reaction, for example.

Expression vectors possess partial sequences which are capable of replicating in host organisms optimized for production of proteins and of bringing the gene contained there to expression. Expression vectors are preferred as they carry the genetic elements necessary for expression. Expression, for example, is influenced by promotors which regulate the transcription of the gene. Thus the expression may take place via the natural promotor localized originally in front of this gene but also after genetic-engineered fusion, both via a promotor of the host cell prepared on the expression vector and also via a modified or totally different promotor of another organism.

Also preferred are expression vectors which are capable of being regulated by changes in the culture conditions or by addition of certain compounds, e.g., the cell density or special factors. Expression vectors make it possible for the corresponding protein to be produced heterologously, therefore in a different organism than that from which it can be obtained naturally. Also a homologous protein acquisition from a host organism expressing the gene naturally via a suitable vector lies within the scope of protection of the present invention. This may have the advantage that natural modification reactions related to the translation can be performed precisely on the protein which forms in the same manner as they would take place naturally.

To recover the polypeptide according to the invention, microorganisms transformed by an expression vector containing structures coding for the corresponding enzyme are cultivated. The expression vectors in this case were obtained by processes to be described later. The especially preferred microorganisms that were transformed with the expression vector are: *Saccharomyces cerevisiae* and *Pichi pastoris*. Preferred vectors are plasmids whose restriction maps are shown in FIGS. 1-3.

Among the vectors used within the scope of the invention are those which are formed by cutting with suitable restriction endonucleases, preferably BamHI or SnaBI and subsequent recombination with the corresponding N or C terminal halves of the enzyme structure gene. Restriction endonucleases are enzymes which substrate-specifically decompose double-strand DNA into fragments by splitting the phosphate diester bonds between the individual nucleotide building blocks of the DNA. All restriction endonucleases are capable of recognizing certain base sequences of the DNA which mark specific action sites (interfaces) for the activity of the corresponding endonucleases. Upon cutting (restriction) of double-strand DNA in the case of some endonucleases, specific so-called "protruding ends" are formed which, under certain conditions of renaturation, are capable of joining with each other again (recombination) or with the corresponding (complementary) protruding ends of DNA fragments (ligated) obtained by a different route.

Cell-free expression systems in which the protein biosynthesis takes place in vitro are also within the scope of the invention. Such expression systems are also state of the art.

Host cells containing one of the above-defined vectors, especially a cloning or an expression vector are also encompassed by the present invention. Vector transformation into corresponding cells takes place in the course of molecular-biological operations such as are necessary, e.g., for mutagenesis, sequencing or storage of the vectors. Depending on the method, for example, here gram-positive, but especially also gram-negative bacteria may be suitable for this. Such host cells are useful for producing the lipase/acyltransferase of the invention.

The preferred in-vivo synthesis of a polypeptide according to the invention requires the transfer of the corresponding gene to a host cell. As host cells, basically all organisms are suitable, i.e. prokaryotes, eukaryotes, or cyanophyta. Host cells which can be readily manipulated genetically, for example, by transformation with the expression vector and its stable establishment, e.g., single-cell fungi or bacteria are particularly preferred. Preferred host cells are characterized by good microbiological and biotechnological manipulability. This means easily cultured, high growth rates, low fermentation media requirements, and good rates of production and secretion of foreign proteins.

Expression systems in which additional genes, e.g., those made available on other vectors, influence the production of proteins are within the invention. In this case modified gene products may be involved or those that are to be purified together with the protein according to the invention, perhaps to influence its function. This may involve, e.g., other proteins or enzymes, inhibitors or elements influencing interaction with different substrates. Preferred host cells are prokaryote or bacterial cells. Bacteria are distinguished from eukaryotes, as a rule, by shorter generation times and lower demands on culture conditions. As a result economical processes may be set up for obtaining the proteins according to the invention.

Heterologous expression is preferred. Gram-positive bacteria such as actinomycetes or bacilli have no external membrane so that they release the secreted proteins directly into the medium surrounding them. Among the bacteria preferred for heterologous expression are therefore those of the genus *Bacillus*, especially those of the species listed below.

Gram-negative bacterial, i.e., those of the genera *Klebsiella* or *Escherichia*, may also be used for heterologous expression. In these bacteria, a large number of proteins are secreted into the periplasmatic space, i.e. the compartment between the two membranes enclosing the cells. This may be advantageous for certain applications.

Eukaryote cells may also be suitable for the production of polypeptides according to the invention. Examples of these are yeasts, such as *Saccharomyces* or *Kluyveromyces*. This may be especially advantageous, for example, when post-translational modification is required for proper enzyme function or correct targeting in the protein secretion pathway. The proteins are to undergo modifications in connection with their synthesis to make such host expression systems possible. These include, for example, the binding of compounds, such as acyl groups which serve as membrane anchors, or oligosaccharides, which may determine immunogenic properties.

Especially preferred for production of polypeptides according to the invention from transformed host cells are microorganisms which are selected from the group consisting of *Candida parapsilosis, Saccharomyces cerevisiae, Schizosaccharomyces pombe, Pichia pastoris, Pichia boidinii, Pichia stipitis, Hansenula polymorpha, Kluyveromyces lactis, Schwanniomyces castellii, Yarrowia lipolytica, Escherichia coli, Bacillus subtilis, Bacillus amylolichefaciens, Bacillus stearothermophilus, Bacillus licheniformis, Lactococcus lactis, Streptococcus lactis, Lactobacillus bulgaricus, Aspergillus oryzae, Aspergillus niger, Trichoderma reesei, Mucor* sp. and *Rhizopus* sp.

The transformed host cells, also called transformants, are subsequently cultured by known methods, preferably as in the examples, and the polypeptides produced according to the invention are isolated.

In an exemplary process for producing the nucleic acids according to the invention, that is, nucleic acids with the above-defined similarity and sequence identities to the sequences of SEQ ID NO 1 or SEQ ID NO 3, are operably linked in a suitable nucleic acid expression vector. The latter is transferred into the host cell, e.g., into cells of an easily cultured bacterial or yeast strain which secretes the proteins, whose genes are under the control of the appropriate genetic elements (i.e., promoters), into the surrounding nutrient medium; regulating elements for this may be made available, e.g., from the expression vector. From the surrounding medium the protein according to the invention can be isolated by several purification steps such as precipitation or chromatography. One of ordinary skill in the art is able to scale-up a system that has been optimized experimentally on the laboratory scale to the scale of industrial production.

The discovery of new enzymes is also called screening. In particular one screens the gene banks of certain organism following general methods, such as are reported in Fritsch, Sambrook and Maniatis: "Molecular Cloning: A Laboratory Manual," Cold Spring Harbor Laboratory Press, NY, 1989.

By comparison with known enzymes which are on file, e.g., in generally available data banks, from the amino acid or nucleotide sequence which are characteristic to certain molecular structures, such as domain elements, the enzymatic activity of an enzyme in question may be inferred. Such a comparison is accomplished by coordinating similar sequences in the nucleotide or amino acid sequences of the proteins being analyzed with each other. This is called "homologizing." A tabular classification of the positions involved is called an "alignment." In the analysis of nucleotide sequences, in turn, both complementary strands of all three possible reading grids are to be taken into account. Likewise, the degenerateness of the genetic code and the organism-specific codon usage must be considered. Alignments may be prepared by computer program, such as the algorithms FASTA or BLAST; this procedure is described, e.g., by D. J. Lipman and W. R. Pearson (1985) in Science, vol. 227, p 1435-1441. A comparison of all positions in agreement in the sequences compared is called "consensus sequence."

Such a comparison also permits an assessment to be made regarding the similarity or homology of the sequences being compared with each other. This is reported in "per cent identity," i.e. the content of identical nucleotides or amino acid residues in the same positions. Another homology definition relates the preserved amino acid exchanges in this value to unity. One then speaks of "per cent similarity." The degree of sequence similarity or identity can be evaluated with respect to the entire putative gene, or to subsequences encompassing parts of the gene, such as those that code for the catalytic site of the enzyme, for example.

Homologous regions of different proteins are usually those with the same structural elements and/or functions which may be recognized by similarities in the primary amino acid sequence. It ranges up to full identities in the smallest regions, so-called boxes, which include only a few amino acids and usually exercise essential functions for the overall activity, and therefore show little if any variation among homologous proteins. The term "functions of the homologous regions" are to be understood to mean the smallest partial functions of the function exhibited by the protein, such as, e.g., the individual residues directly participating in the formation of individual hydrogen bridge bonds for complexing a substrate or transition complex.

Based on alignments, essentially the same secondary and tertiary structures may be assumed for polypeptides according to the invention as for the proteins used for homologization. Their structural elements can generally be called up in the generally accessible data banks, such as that at the EMBL-European Bioinformatics Institute (EBI) in Cambridge, Great Britain (http://www.ebi.ac.uk), Swiss-Prot. or GenBank (National Center for Biotechnology Information, NCB, National Institutes of Health, Bethesda, USA.). If structures deviating from them should arise or if it should be found that different folding variants exist with varying properties, which impacts or influences some functions or aspects of enzyme activity, e.g., the optimal reaction conditions or substrate specificity, then all of these are included within the scope of the present invention. As another example, correct protein folding may depend on the production conditions (pH, ionic strength, etc.), and on the presence or absence of the leader peptide signaling sequence to target the protein to certain compartments of the cell such as the endoplasmic reticulum of Golgi apparatus. These variants or possibilities for creating such variants may be useful for engineering properties of the enzyme that are useful in certain applications Another subject of the invention is the application of polypeptides described as catalysts in acyl transfer reactions, especially in reactions selected from the group formed by alcoholysis of esters, especially glycerols or sterols, alcoholysis of thio esters, thiolysis of esters, aminolysis of an ester with hydroxylamines or hydrazines; reaction of an ester with hydrogen peroxides and enantioselective synthesis of esters, thioesters or lactones by alcoholysis. Special reactions which are catalyzed by the polypeptides according to the invention are described, e.g., in a) Fournand, et al., J. Mol. Catalysis B, 1998, 5, 207-211; b) Briand, et al., Eur. J. Biochem. 1995, 228, 169-75.

The following examples are provided to illustrate certain embodiments of the present invention. They are not intended to limit the scope of the invention in any way.

EXAMPLES

Example 1

Cultivation of the Strain and Isolation of the Polypeptide

The strain *Candida parapsilosis* (Ashford) Langeron and Tallice, CBS 604, was deposited at the Centraalbureau voor Schimmelcultures, Yeast Division, Delft, Netherlands.

The cultivation was carried out in the same manner as in Briand, et al., Eur. J. Biochem. 1995, 228, 169-175. The main culture was adjusted to pH 6.5 with 100 mM phosphate buffer and mixed with 5 g/l glucose as the C source.

At the end of the exponential growth phase the culture broth was centrifuged (7000 g for 15 min) and the lipase/acyltransferase obtained from the supernatant fluid. The polypeptide was purified by the method described in Riaublanc, A., et al., J. Am. Oil Chem. Soc. 1993, 70, 497-500.

Example 2

Molecular-biological Operating Steps

All moleculabiology techniques follow standard methods such as are reported in the manuals such as that of Fritsch, Sambrook, and Maniatis, "Molecular Cloning: A laboratory manual," Cold Spring Harbor Laboratory Press, NY, 1989.

The content of lipase/acyltransferase was measured in units (U) determined as the content of oleic acid that was obtained per minute during the hydrolysis of trioleyl glycerol under the conditions described in Briand et al., in Eur. J. Biochem. 1995, 228, 169-175. The protein concentration was determined by the method of Bradford (1976, Anal. Biochem. 72, 248-254).

Example 3

Expression of a Gene Containing the Nucleic Acid Per SEQ ID NO 1 in *Saccharomyces Cerevisiae*

For expression of the desired nucleic acid sequence, the DNA was partially hydrolyzed with the restriction endonuclease BamHI. Degenerate(?) PCR primers were constructed which contained the nucleic acid per SEQ ID NO 1. The following primer pairs were used (start and stop codon are underlined, BamHI restriction side is printed in bold face type): The forward primer is SEQ ID NO: 5 and the reverse primer is SEQ ID NO: 6.

forward 5'-CTCGGATCC<u>ATG</u>CGTTACMTTTGCTATTGC reverse 5'-CACGGATCC<u>TTA</u>AAAAGCAAAACGTTCCA ACTTGAGCAATCC The following time/temperature program was carried out for PCR amplification: 5 min at 95° C. denaturing and then 30 cycles of 1 min at 95° C., 1 min at 50° C., 1 min at 72° C. and as the last step 10 min at 72° C.

The fragments from the PCR were digested with the restriction endonuclease BamHI and subsequently ligated into the vector pVT100-U cut with the restriction endonuclease BamHI to form the recombinant plasmid. The vector pVT100CpLIP2 shown in FIG. 1 (replicative plasmid) was obtained. The absence of mutations was verified by sequencing the insert. The transformation of the newly combined DNA into the strain *Saccharomyces cerevisiae* W303-1a was performed by the electroporation method described by Becker et al. in Methods in Enzymology, 1991, 194, 182-187. The transformants were selected on YNB medium without uracil (6.7 g/l Yeast Nitrogen Base without amino acid by Difco, 20 g/l glucose, 150 mg/l leucine, 100 mg/l adenine, 100 mg/l histidine, 100 mg/l tryptophan) with a frequency of $1-2\times10^4$ transformants per μg of DNA. The transformants were selected in a plate test for lipase activity by the method of Kouker described in: Kouker, G., et al., Applied Environ. Microbiol. 1987, 59, 211-213.

The selected transformant was cultured in a shaker bottle at 28° C. in YPD medium (YPD=10 g/l yeast extract by Difco, 20 g/l Bacto Peptone [Difco], 60 g/l glucose, 150 mg/l leucine, 100 mg/l adenine, 100 mg/l histidine and 100 mg/l tryptophan). The culture broth was harvested after 36 h of fermentation, and the supernatant of the culture was separated from the residue by centrifugation. The supernatant contained 2500 U of the recombinant lipase/acyltransferase per liter and a specific activity of 0.7 U/mg. After concentrating by ultrafiltration and hydrophobic chromatography on phenylsepharose 6 Fast-Flow gel, 10% of the activity could be recovered with a specific activity of 80 U/mg.

Example 4

Expression of a Gene Containing SEQ ID NO 1 in *Pichia pastoris*

The lipase/acyltransferase was expressed as fusion to an N terminal peptide which coded for the secretion signal of the a factor from *Saccharomyces cerevisiae*. First the gene corresponding to SEQ ID NO 1 PCR was amplified and in this way a cut(truncated?) gene of the mature gene was obtained. The following primers were used: (the stop codon is underlined, the first phenylalanine codon of the mature gene is printed in boldface type). The forward primer is SEQ ID NO: 7 and the reverse primer is SEQ ID NO: 8.
forward 5'-TTTGTCTTGGCTCCCAAAAAGCCA
reverse 5'-TTAAAAAGCAAAACGTTCCAACTTGAGCAATCC The following time/temperature program was executed for PCR amplification: 2 min at 94° C. denaturing and then 15 cycles of 15 sec at 94° C., 30 sec at 50° C., 90 sec at 72° C. plus 5 sec per cycle for the extension period of cycle 11, and as the last step, 7 min at 72° C.

After amplification the fragment obtained was phosphorylated with T4 polynucleotide lipase and a blunt end was added with T4-DNA polymerase. The fragment was then ligated to a pPIC9K plasmid digested by SnaBI, and the vector pPIC9KCpLIP2 (replicative plasmid) was obtained (FIG. 2). The absence of mutations was verified by sequencing the insert.

The transformation of the yeast spheroplasts was performed with the Pichia expression kit by the Invitrogen Co. (Groningen, Netherlands). The transformation frequency was $10^3$ transformations per μg of DNA.

A selected transformant was cultivated in a fermenter with a synthetic (?) described by Boze et al. in: Boze, H., et al., Process Biochem. 2001, 36, 907-913) to which 40 g/l glycerol had been added. After the growth phase (after 2500 min. of fermentation) in the batch process pure methanol (5 g/l) was added in the sub-batch process in order to induce the expression of the gene. After four days of cultivation with a high cell density the supernatant of the culture broth is separated from the residue by centrifugation. The supernatant obtained contained 102000 U/l of recombinant lipaseacyltransferase with a specific activity of 80 U/mg of protein. Concentration by ultrafiltration with 10000 kD cut-off membranes produced an enzyme concentration of 830000 U/l with a specific activity of 150 U/mg.

Example 5

Expression of a Modified (His-tagged) Lipase/Acyltransferase in *Saccharomyces Cerevisiae*

In order to express the modified desired nucleic acid sequence per SEQ ID NO 3 which makes possible the fusion of 6-His-peptide to the C-terminal end of the sequence of the polypeptide per SEQ ID NO 2, first DNA was partially hydrolyzed with the restriction endonuclease BamHI. Primers were constructed by PCR which contained part of the nucleic acid per SEQ ID NO 1. The following primer pairs, which are made with an extension of the nucleic acid sequence with 6 histidine codons, were used (start and stop codon are underlined, BamHI restriction side printed in boldface type, his codons are printed in italics): The forward primer is SEQ ID NO:9 and the reverse primer is SEQ ID NO: 10.
forward 5'-CTCGGATCC<u>ATG</u>CGTTACTTTGCTATTGC
reverse 5'-CACGGATCC<u>TTA</u>ATGATGATGATGATGAT GAAAAGCAAAACGTTCCAACTTGAGCAATCC The following time/temperature program was carried out for PCR amplification: denaturing for 5 min at 95° C. and then 30 cycles of 1 min at 95° C., 1 min at 50° C., 1 min at 72° C., and as the last step 10 min at 72° C.

The fragments from PCR were digested with the restriction endonuclease BamHI and subsequently ligated to the plasmid in the vector pVT100-U cut with the restriction endonuclease BamHI. The vector pVT100CpLIP2His in FIG. 3 (integrative plasmid) was obtained. The transformation of *Saccharomyces cerevisiae* W303-1a and the expression of the gene were carried out according to example 3.

The transformant selected was cultivated in shaker bottles at 28° C. in YPD medium (YPD=10 g/l yeast extract [Difco], 20 g/l Bacto Peptone [Difco], 60 g/l glucose, 150 mg/l leucine, 100 mg/l adenine, 100 mg/l histidine, and 100 mg/l tryptophan). The culture broth was harvested after 36 hours of fermentation, and the supernatant of the culture solution was separated from the residue by centrifugation. The supernatant was found to contain 3100 U of the recombinant his-tagged lipase/acyltransferase per liter and had a specific activity of 0.25 U/mg of protein. Ion-chelating properties were utilized for purification in a one step process. For this purpose Ni-nitrilotriacetic acid agarose affinity gels supplied by the Qiagen Co. were used as described by the manufacturer. 26% of the enzyme was (recovered) with a specific activity 150 U/mg of protein.

What is claimed is:

1. An isolated polypeptide comprising SEQ ID NO:2 which has lipase/acyltransferase activity.

2. An isolated polypeptide variant having lipase/acyltransferase activity wherein the variant polypeptide comprises amino acids 190–390 of SEQ ID NO: 2 or wherein the variant polypeptide comprises a sequence which is 96% identical to amino acids 190-390 of SEQ ID NO: 2 said polypeptide optionally comprising an additional polypeptide sequence and optionally being glycosylated.

3. The isolated polypeptide of claim 1 consisting of SEQ ID NO: 2, said polypeptide having lipase/acyltransferase activity.

4. The polypeptide of claim 1, which is glycosylated.

5. The isolated polypeptide of claim 2, which is glycosylated.

6. The polypeptide of claim 1 comprising an additional peptide sequence.

7. The polypeptide of claim 6, wherein said additional peptide encodes a marker.

8. The polypeptide of claim 6, having the sequence of SEQ ID NO: 4, wherein said additional peptide sequence comprises a his tag.

9. The polypeptide of claim 8, which is glycosylated.

10. The polypeptide of claim 1, which is isolated from a microorganism.

11. The polypeptide of claim 10, wherein said microorganism is a fungus.

12. The polypeptide of claim 11, wherein said fungus is selected from the group consisting of *Candida parapsilosis, Candida antarctica, Trychosporon oryzae, Pseudozyma Antarctica, Candida glabrata, Candida albicans, Candida maltosa, Candida tropicalis, Candida viswanathii, Issatchenkia orientalis, Candida krusel, Kluyveromyces marxianus, C. kefyr, C. pseudotropicalis, Pichia guilliermondil, Candida guilliermondii, Geotrichum candidum, Fusarium solani* and *Aeromonas aerophila*.

13. A polypeptide as claimed in claim 2, which catalyzes a reaction selected from the group consisting of alcoholysis of esters, alcoholysis of thio esters, thiolysis of esters, aminolysis of an ester with hydroxylamines or hydrazines, reaction of an ester with hydrogen peroxides and enantioselective synthesis of esters, thioesters, and lactones by alcoholysis.

* * * * *

SEQUENCE LISTING

<160> NUMBER OF SEQ ID NOS: 10

<210> SEQ ID NO 1
<211> LENGTH: 1398
<212> TYPE: DNA
<213> ORGANISM: Candida parapsilosis
<220> FEATURE:
<221> NAME/KEY: CDS
<222> LOCATION: (1)...(1398)

<400> SEQUENCE: 1

| | | | | | | | | | | | | | | | | |
|---|---|---|---|---|---|---|---|---|---|---|---|---|---|---|---|---|
| atg | cgt | tac | ttt | gct | att | gct | ttc | ttg | ctc | atc | aat | acc | att | tca | gct | 48 |
| Met | Arg | Tyr | Phe | Ala | Ile | Ala | Phe | Leu | Leu | Ile | Asn | Thr | Ile | Ser | Ala | |
| 1 | | | | 5 | | | | | 10 | | | | | 15 | | |
| ttt | gtc | ttg | gct | ccc | aaa | aag | cca | tct | caa | gac | gat | ttc | tac | act | cca | 96 |
| Phe | Val | Leu | Ala | Pro | Lys | Lys | Pro | Ser | Gln | Asp | Asp | Phe | Tyr | Thr | Pro | |
| | | | 20 | | | | | 25 | | | | | 30 | | | |
| cca | caa | ggt | tat | gaa | gct | caa | cct | ctt | ggt | tct | att | ttg | aaa | aca | aga | 144 |
| Pro | Gln | Gly | Tyr | Glu | Ala | Gln | Pro | Leu | Gly | Ser | Ile | Leu | Lys | Thr | Arg | |
| | | 35 | | | | | 40 | | | | | 45 | | | | |
| aac | gtc | ccc | aat | cca | ttg | act | aat | gtt | ttc | act | cca | gtt | aaa | gtt | caa | 192 |
| Asn | Val | Pro | Asn | Pro | Leu | Thr | Asn | Val | Phe | Thr | Pro | Val | Lys | Val | Gln | |
| | 50 | | | | | 55 | | | | | 60 | | | | | |
| aat | gca | tgg | caa | tta | ttg | gtt | aga | tct | gaa | gat | aca | ttt | ggt | aac | cca | 240 |
| Asn | Ala | Trp | Gln | Leu | Leu | Val | Arg | Ser | Glu | Asp | Thr | Phe | Gly | Asn | Pro | |
| 65 | | | | | 70 | | | | | 75 | | | | | 80 | |
| aac | gcc | ata | gtc | act | acc | att | att | caa | cct | ttc | aat | gct | aaa | aag | gat | 288 |
| Asn | Ala | Ile | Val | Thr | Thr | Ile | Ile | Gln | Pro | Phe | Asn | Ala | Lys | Lys | Asp | |
| | | | | 85 | | | | | 90 | | | | | 95 | | |
| aag | ctt | gtt | tct | tat | caa | aca | ttt | gaa | gat | tct | ggt | aaa | ttg | gat | tgt | 336 |
| Lys | Leu | Val | Ser | Tyr | Gln | Thr | Phe | Glu | Asp | Ser | Gly | Lys | Leu | Asp | Cys | |
| | | | 100 | | | | | 105 | | | | | 110 | | | |
| gct | cca | tca | tat | gct | att | caa | tat | gga | tcg | gac | att | tcg | act | ttg | acc | 384 |
| Ala | Pro | Ser | Tyr | Ala | Ile | Gln | Tyr | Gly | Ser | Asp | Ile | Ser | Thr | Leu | Thr | |
| | | 115 | | | | | 120 | | | | | 125 | | | | |
| act | caa | ggt | gaa | atg | tac | tac | atc | tct | gct | tta | tta | gat | caa | ggt | tac | 432 |
| Thr | Gln | Gly | Glu | Met | Tyr | Tyr | Ile | Ser | Ala | Leu | Leu | Asp | Gln | Gly | Tyr | |
| | 130 | | | | | 135 | | | | | 140 | | | | | |
| tat | gtt | gtc | act | cct | gat | tac | gag | ggt | cca | aag | agt | aca | ttc | act | gta | 480 |
| Tyr | Val | Val | Thr | Pro | Asp | Tyr | Glu | Gly | Pro | Lys | Ser | Thr | Phe | Thr | Val | |
| 145 | | | | | 150 | | | | | 155 | | | | | 160 | |
| ggg | ttg | caa | tca | gga | aga | gct | act | ttg | aat | tcg | ctt | aga | gct | act | ttg | 528 |
| Gly | Leu | Gln | Ser | Gly | Arg | Ala | Thr | Leu | Asn | Ser | Leu | Arg | Ala | Thr | Leu | |
| | | | | 165 | | | | | 170 | | | | | 175 | | |
| aaa | tca | gga | aac | ttg | act | ggt | gtt | tca | tca | gac | gct | gag | aca | tta | ttg | 576 |
| Lys | Ser | Gly | Asn | Leu | Thr | Gly | Val | Ser | Ser | Asp | Ala | Glu | Thr | Leu | Leu | |
| | | | 180 | | | | | 185 | | | | | 190 | | | |
| tgg | ggt | tat | tca | gga | gga | agt | ctt | gct | tca | gga | tgg | gct | gct | gct | ata | 624 |
| Trp | Gly | Tyr | Ser | Gly | Gly | Ser | Leu | Ala | Ser | Gly | Trp | Ala | Ala | Ala | Ile | |
| | | 195 | | | | | 200 | | | | | 205 | | | | |
| caa | aaa | gaa | tat | gct | cca | gag | ttg | agt | aaa | aac | ttg | ctt | ggt | gct | gca | 672 |
| Gln | Lys | Glu | Tyr | Ala | Pro | Glu | Leu | Ser | Lys | Asn | Leu | Leu | Gly | Ala | Ala | |
| | 210 | | | | | 215 | | | | | 220 | | | | | |
| ctt | ggt | gga | ttc | gtt | aca | aac | att | act | gcc | act | gct | gaa | gct | gtt | gat | 720 |
| Leu | Gly | Gly | Phe | Val | Thr | Asn | Ile | Thr | Ala | Thr | Ala | Glu | Ala | Val | Asp | |
| 225 | | | | | 230 | | | | | 235 | | | | | 240 | |
| agt | ggt | cca | ttt | gca | gga | atc | atc | tcc | aat | gca | ttg | gct | ggt | att | gga | 768 |
| Ser | Gly | Pro | Phe | Ala | Gly | Ile | Ile | Ser | Asn | Ala | Leu | Ala | Gly | Ile | Gly | |
| | | | | 245 | | | | | 250 | | | | | 255 | | |

| | | |
|---|---|---|
| aat gaa tac cct gat ttc aaa aac tat ctt ttg aaa aaa gtg tca cca | | 816 |
| Asn Glu Tyr Pro Asp Phe Lys Asn Tyr Leu Leu Lys Lys Val Ser Pro | | |
| 260 265 270 | | |
| ttg ctt tca atc act tat cgt ttg gga aac act cac tgt ttg ctt gat | | 864 |
| Leu Leu Ser Ile Thr Tyr Arg Leu Gly Asn Thr His Cys Leu Leu Asp | | |
| 275 280 285 | | |
| ggt ggt att gct tat ttc ggt aaa tca ttc ttt tcc aga att att aga | | 912 |
| Gly Gly Ile Ala Tyr Phe Gly Lys Ser Phe Phe Ser Arg Ile Ile Arg | | |
| 290 295 300 | | |
| tat ttc cct gat gga tgg gat ctt gtc aac caa gaa cct atc aaa acc | | 960 |
| Tyr Phe Pro Asp Gly Trp Asp Leu Val Asn Gln Glu Pro Ile Lys Thr | | |
| 305 310 315 320 | | |
| atc ttg caa gat aat gga ttg gtt tac caa cca aag gac ttg acc cca | | 1008 |
| Ile Leu Gln Asp Asn Gly Leu Val Tyr Gln Pro Lys Asp Leu Thr Pro | | |
| 325 330 335 | | |
| caa att cca tta ttc atc tac cac ggt acc ttg gat gca att gtc ccc | | 1056 |
| Gln Ile Pro Leu Phe Ile Tyr His Gly Thr Leu Asp Ala Ile Val Pro | | |
| 340 345 350 | | |
| att gtc aac tca aga aag aca ttc caa caa tgg tgt gat tgg gga ctc | | 1104 |
| Ile Val Asn Ser Arg Lys Thr Phe Gln Gln Trp Cys Asp Trp Gly Leu | | |
| 355 360 365 | | |
| aaa tct ggt gaa tat aat gaa gat ttg acc aat gga cac att act gaa | | 1152 |
| Lys Ser Gly Glu Tyr Asn Glu Asp Leu Thr Asn Gly His Ile Thr Glu | | |
| 370 375 380 | | |
| tca att gtg ggt gca cca gct gct ttg act tgg att atc aat cgt ttc | | 1200 |
| Ser Ile Val Gly Ala Pro Ala Ala Leu Thr Trp Ile Ile Asn Arg Phe | | |
| 385 390 395 400 | | |
| aat gga cag cct cca gtt gat gga tgt caa cat aat gtg aga gct tca | | 1248 |
| Asn Gly Gln Pro Pro Val Asp Gly Cys Gln His Asn Val Arg Ala Ser | | |
| 405 410 415 | | |
| aac ttg gaa tat cca gga act cca caa tca atc aag aat tac ttt gaa | | 1296 |
| Asn Leu Glu Tyr Pro Gly Thr Pro Gln Ser Ile Lys Asn Tyr Phe Glu | | |
| 420 425 430 | | |
| gct gca ttg cac gca att ttg ggc ttt gat ttg ggt cca gat gtt aag | | 1344 |
| Ala Ala Leu His Ala Ile Leu Gly Phe Asp Leu Gly Pro Asp Val Lys | | |
| 435 440 445 | | |
| aga gat aag gtt act ttg ggc gga ttg ctc aag ttg gaa cgt ttt gct | | 1392 |
| Arg Asp Lys Val Thr Leu Gly Gly Leu Leu Lys Leu Glu Arg Phe Ala | | |
| 450 455 460 | | |
| ttt tag | | 1398 |
| Phe * | | |
| 465 | | |

<210> SEQ ID NO 2
<211> LENGTH: 465
<212> TYPE: PRT
<213> ORGANISM: Candida parapsilosis

<400> SEQUENCE: 2

Met Arg Tyr Phe Ala Ile Ala Phe Leu Leu Ile Asn Thr Ile Ser Ala
1               5                   10                  15

Phe Val Leu Ala Pro Lys Lys Pro Ser Gln Asp Asp Phe Tyr Thr Pro
            20                  25                  30

Pro Gln Gly Tyr Glu Ala Gln Pro Leu Gly Ser Ile Leu Lys Thr Arg
        35                  40                  45

Asn Val Pro Asn Pro Leu Thr Asn Val Phe Thr Pro Val Lys Val Gln
    50                  55                  60

Asn Ala Trp Gln Leu Leu Val Arg Ser Glu Asp Thr Phe Gly Asn Pro
65                  70                  75                  80

```
Asn Ala Ile Val Thr Ile Ile Gln Pro Phe Asn Ala Lys Lys Asp
                 85              90              95

Lys Leu Val Ser Tyr Gln Thr Phe Glu Asp Ser Gly Lys Leu Asp Cys
                100             105             110

Ala Pro Ser Tyr Ala Ile Gln Tyr Gly Ser Asp Ile Ser Thr Leu Thr
            115             120             125

Thr Gln Gly Glu Met Tyr Tyr Ile Ser Ala Leu Leu Asp Gln Gly Tyr
        130             135             140

Tyr Val Val Thr Pro Asp Tyr Glu Gly Pro Lys Ser Thr Phe Thr Val
145             150             155             160

Gly Leu Gln Ser Gly Arg Ala Thr Leu Asn Ser Leu Arg Ala Thr Leu
                165             170             175

Lys Ser Gly Asn Leu Thr Gly Val Ser Ser Asp Ala Glu Thr Leu Leu
            180             185             190

Trp Gly Tyr Ser Gly Gly Ser Leu Ala Ser Gly Trp Ala Ala Ala Ile
        195             200             205

Gln Lys Glu Tyr Ala Pro Glu Leu Ser Lys Asn Leu Leu Gly Ala Ala
    210             215             220

Leu Gly Gly Phe Val Thr Asn Ile Thr Ala Thr Ala Glu Ala Val Asp
225             230             235             240

Ser Gly Pro Phe Ala Gly Ile Ile Ser Asn Ala Leu Ala Gly Ile Gly
                245             250             255

Asn Glu Tyr Pro Asp Phe Lys Asn Tyr Leu Leu Lys Lys Val Ser Pro
            260             265             270

Leu Leu Ser Ile Thr Tyr Arg Leu Gly Asn Thr His Cys Leu Leu Asp
275             280             285

Gly Gly Ile Ala Tyr Phe Gly Lys Ser Phe Ser Arg Ile Ile Arg
        290             295             300

Tyr Phe Pro Asp Gly Trp Asp Leu Val Asn Gln Glu Pro Ile Lys Thr
305             310             315             320

Ile Leu Gln Asp Asn Gly Leu Val Tyr Gln Pro Lys Asp Leu Thr Pro
                325             330             335

Gln Ile Pro Leu Phe Ile Tyr His Gly Thr Leu Asp Ala Ile Val Pro
            340             345             350

Ile Val Asn Ser Arg Lys Thr Phe Gln Gln Trp Cys Asp Trp Gly Leu
        355             360             365

Lys Ser Gly Glu Tyr Asn Glu Asp Leu Thr Asn Gly His Ile Thr Glu
    370             375             380

Ser Ile Val Gly Ala Pro Ala Ala Leu Thr Trp Ile Ile Asn Arg Phe
385             390             395             400

Asn Gly Gln Pro Pro Val Asp Gly Cys Gln His Asn Val Arg Ala Ser
                405             410             415

Asn Leu Glu Tyr Pro Gly Thr Pro Gln Ser Ile Lys Asn Tyr Phe Glu
            420             425             430

Ala Ala Leu His Ala Ile Leu Gly Phe Asp Leu Gly Pro Asp Val Lys
        435             440             445

Arg Asp Lys Val Thr Leu Gly Gly Leu Leu Lys Leu Glu Arg Phe Ala
450             455             460

Phe
465
```

```
<210> SEQ ID NO 3
<211> LENGTH: 1416
<212> TYPE: DNA
<213> ORGANISM: Candida parapsilosis
<220> FEATURE:
<221> NAME/KEY: CDS
<222> LOCATION: (1)...(1416)

<400> SEQUENCE: 3 atg cgt tac ttt gct att gct ttc ttg ctc atc aat acc att tca gct      48
Met Arg Tyr Phe Ala Ile Ala Phe Leu Leu Ile Asn Thr Ile Ser Ala
 1               5                  10                  15 ttt gtc ttg gct ccc aaa aag cca tct caa gac gat ttc tac act cca      96
Phe Val Leu Ala Pro Lys Lys Pro Ser Gln Asp Asp Phe Tyr Thr Pro
             20                  25                  30 cca caa ggt tat gaa gct caa cct ctt ggt tct att ttg aaa aca aga     144
Pro Gln Gly Tyr Glu Ala Gln Pro Leu Gly Ser Ile Leu Lys Thr Arg
         35                  40                  45 aac gtc ccc aat cca ttg act aat gtt ttc act cca gtt aaa gtt caa     192
Asn Val Pro Asn Pro Leu Thr Asn Val Phe Thr Pro Val Lys Val Gln
     50                  55                  60 aat gca tgg caa tta ttg gtt aga tct gaa gat aca ttt ggt aac cca     240
Asn Ala Trp Gln Leu Leu Val Arg Ser Glu Asp Thr Phe Gly Asn Pro
 65                  70                  75                  80 aac gcc ata gtc act acc att att caa cct ttc aat gct aaa aag gat     288
Asn Ala Ile Val Thr Thr Ile Ile Gln Pro Phe Asn Ala Lys Lys Asp
                 85                  90                  95 aag ctt gtt tct tat caa aca ttt gaa gat tct ggt aaa ttg gat tgt     336
Lys Leu Val Ser Tyr Gln Thr Phe Glu Asp Ser Gly Lys Leu Asp Cys
            100                 105                 110 gct cca tca tat gct att caa tat gga tcg gac att tcg act ttg acc     384
Ala Pro Ser Tyr Ala Ile Gln Tyr Gly Ser Asp Ile Ser Thr Leu Thr
        115                 120                 125 act caa ggt gaa atg tac tac atc tct gct tta tta gat caa ggt tac     432
Thr Gln Gly Glu Met Tyr Tyr Ile Ser Ala Leu Leu Asp Gln Gly Tyr
    130                 135                 140 tat gtt gtc act cct gat tac gag ggt cca aag agt aca ttc act gta     480
Tyr Val Val Thr Pro Asp Tyr Glu Gly Pro Lys Ser Thr Phe Thr Val
145                 150                 155                 160 ggg ttg caa tca gga aga gct act ttg aat tcg ctt aga gct act ttg     528
Gly Leu Gln Ser Gly Arg Ala Thr Leu Asn Ser Leu Arg Ala Thr Leu
                165                 170                 175 aaa tca gga aac ttg act ggt gtt tca tca gac gct gag aca tta ttg     576
Lys Ser Gly Asn Leu Thr Gly Val Ser Ser Asp Ala Glu Thr Leu Leu
            180                 185                 190 tgg ggt tat tca gga gga agt ctt gct tca gga tgg gct gct gct ata     624
Trp Gly Tyr Ser Gly Gly Ser Leu Ala Ser Gly Trp Ala Ala Ala Ile
        195                 200                 205 caa aaa gaa tat gct cca gag ttg agt aaa aac ttg ctt ggt gct gca     672
Gln Lys Glu Tyr Ala Pro Glu Leu Ser Lys Asn Leu Leu Gly Ala Ala
    210                 215                 220 ctt ggt gga ttc gtt aca aac att act gcc act gct gaa gct gtt gat     720
Leu Gly Gly Phe Val Thr Asn Ile Thr Ala Thr Ala Glu Ala Val Asp
225                 230                 235                 240 agt ggt cca ttt gca gga atc atc tcc aat gca ttg gct ggt att gga     768
Ser Gly Pro Phe Ala Gly Ile Ile Ser Asn Ala Leu Ala Gly Ile Gly
                245                 250                 255 aat gaa tac cct gat ttc aaa aac tat ctt ttg aaa aaa gtg tca cca     816
Asn Glu Tyr Pro Asp Phe Lys Asn Tyr Leu Leu Lys Lys Val Ser Pro
            260                 265                 270
```

```
ttg ctt tca atc act tat cgt ttg gga aac act cac tgt ttg ctt gat    864
Leu Leu Ser Ile Thr Tyr Arg Leu Gly Asn Thr His Cys Leu Leu Asp
        275                 280                 285 ggt ggt att gct tat ttc ggt aaa tca ttc ttt tcc aga att att aga    912
Gly Gly Ile Ala Tyr Phe Gly Lys Ser Phe Phe Ser Arg Ile Ile Arg
290                 295                 300 tat ttc cct gat gga tgg gat ctt gtc aac caa gaa cct atc aaa acc    960
Tyr Phe Pro Asp Gly Trp Asp Leu Val Asn Gln Glu Pro Ile Lys Thr
305                 310                 315                 320 atc ttg caa gat aat gga ttg gtt tac caa cca aag gac ttg acc cca   1008
Ile Leu Gln Asp Asn Gly Leu Val Tyr Gln Pro Lys Asp Leu Thr Pro
            325                 330                 335 caa att cca tta ttc atc tac cac ggt acc ttg gat gca att gtc ccc   1056
Gln Ile Pro Leu Phe Ile Tyr His Gly Thr Leu Asp Ala Ile Val Pro
        340                 345                 350 att gtc aac tca aga aag aca ttc caa caa tgg tgt gat tgg gga ctc   1104
Ile Val Asn Ser Arg Lys Thr Phe Gln Gln Trp Cys Asp Trp Gly Leu
    355                 360                 365 aaa tct ggt gaa tat aat gaa gat ttg acc aat gga cac att act gaa   1152
Lys Ser Gly Glu Tyr Asn Glu Asp Leu Thr Asn Gly His Ile Thr Glu
370                 375                 380 tca att gtg ggt gca cca gct gct ttg act tgg att atc aat cgt ttc   1200
Ser Ile Val Gly Ala Pro Ala Ala Leu Thr Trp Ile Ile Asn Arg Phe
385                 390                 395                 400 aat gga cag cct cca gtt gat gga tgt caa cat aat gtg aga gct tca   1248
Asn Gly Gln Pro Pro Val Asp Gly Cys Gln His Asn Val Arg Ala Ser
            405                 410                 415 aac ttg gaa tat cca gga act cca caa tca atc aag aat tac ttt gaa   1296
Asn Leu Glu Tyr Pro Gly Thr Pro Gln Ser Ile Lys Asn Tyr Phe Glu
        420                 425                 430 gct gca ttg cac gca att ttg ggc ttt gat ttg ggt cca gat gtt aag   1344
Ala Ala Leu His Ala Ile Leu Gly Phe Asp Leu Gly Pro Asp Val Lys
    435                 440                 445 aga gat aag gtt act ttg ggc gga ttg ctc aag ttg gaa cgt ttt gct   1392
Arg Asp Lys Val Thr Leu Gly Gly Leu Leu Lys Leu Glu Arg Phe Ala
450                 455                 460 ttt cat cat cat cat cat cat taa                                   1416
Phe His His His His His His *
465             470
```

<210> SEQ ID NO 4
<211> LENGTH: 471
<212> TYPE: PRT
<213> ORGANISM: Candida parapsilosis

<400> SEQUENCE: 4

```
Met Arg Tyr Phe Ala Ile Ala Phe Leu Leu Ile Asn Thr Ile Ser Ala
1               5                   10                  15

Phe Val Leu Ala Pro Lys Lys Pro Ser Gln Asp Asp Phe Tyr Thr Pro
                20                  25                  30

Pro Gln Gly Tyr Glu Ala Gln Pro Leu Gly Ser Ile Leu Lys Thr Arg
            35                  40                  45

Asn Val Pro Asn Pro Leu Thr Asn Val Phe Thr Pro Val Lys Val Gln
        50                  55                  60

Asn Ala Trp Gln Leu Leu Val Arg Ser Glu Asp Thr Phe Gly Asn Pro
65                  70                  75                  80

Asn Ala Ile Val Thr Thr Ile Ile Gln Pro Phe Asn Ala Lys Lys Asp
                85                  90                  95
```

-continued

```
Lys Leu Val Ser Tyr Gln Thr Phe Glu Asp Ser Gly Lys Leu Asp Cys
                100                 105                 110

Ala Pro Ser Tyr Ala Ile Gln Tyr Gly Ser Asp Ile Ser Thr Leu Thr
            115                 120                 125

Thr Gln Gly Glu Met Tyr Tyr Ile Ser Ala Leu Leu Asp Gln Gly Tyr
        130                 135                 140

Tyr Val Thr Pro Asp Tyr Glu Gly Pro Lys Ser Thr Phe Thr Val
145                 150                 155                 160

Gly Leu Gln Ser Gly Arg Ala Thr Leu Asn Ser Leu Arg Ala Thr Leu
                165                 170                 175

Lys Ser Gly Asn Leu Thr Gly Val Ser Ser Asp Ala Glu Thr Leu Leu
            180                 185                 190

Trp Gly Tyr Ser Gly Gly Ser Leu Ala Ser Gly Trp Ala Ala Ile
        195                 200                 205

Gln Lys Glu Tyr Ala Pro Glu Leu Ser Lys Asn Leu Leu Gly Ala Ala
    210                 215                 220

Leu Gly Gly Phe Val Thr Asn Ile Thr Ala Thr Ala Glu Ala Val Asp
225                 230                 235                 240

Ser Gly Pro Phe Ala Gly Ile Ile Ser Asn Ala Leu Ala Gly Ile Gly
                245                 250                 255

Asn Glu Tyr Pro Asp Phe Lys Asn Tyr Leu Leu Lys Lys Val Ser Pro
            260                 265                 270

Leu Leu Ser Ile Thr Tyr Arg Leu Gly Asn Thr His Cys Leu Leu Asp
        275                 280                 285

Gly Gly Ile Ala Tyr Phe Gly Lys Ser Phe Phe Ser Arg Ile Ile Arg
    290                 295                 300

Tyr Phe Pro Asp Gly Trp Asp Leu Val Asn Gln Glu Pro Ile Lys Thr
305                 310                 315                 320

Ile Leu Gln Asp Asn Gly Leu Val Tyr Gln Pro Lys Asp Leu Thr Pro
                325                 330                 335

Gln Ile Pro Leu Phe Ile Tyr His Gly Thr Leu Asp Ala Ile Val Pro
            340                 345                 350

Ile Val Asn Ser Arg Lys Thr Phe Gln Gln Trp Cys Asp Trp Gly Leu
        355                 360                 365

Lys Ser Gly Glu Tyr Asn Glu Asp Leu Thr Asn Gly His Ile Thr Glu
    370                 375                 380

Ser Ile Val Gly Ala Pro Ala Ala Leu Thr Trp Ile Ile Asn Arg Phe
385                 390                 395                 400

Asn Gly Gln Pro Pro Val Asp Gly Cys Gln His Asn Val Arg Ala Ser
                405                 410                 415

Asn Leu Glu Tyr Pro Gly Thr Pro Gln Ser Ile Lys Asn Tyr Phe Glu
            420                 425                 430

Ala Ala Leu His Ala Ile Leu Gly Phe Asp Leu Gly Pro Asp Val Lys
        435                 440                 445

Arg Asp Lys Val Thr Leu Gly Gly Leu Leu Lys Leu Glu Arg Phe Ala
    450                 455                 460

Phe His His His His His
465                 470
```

<210> SEQ ID NO 5
<211> LENGTH: 29
<212> TYPE: DNA
<213> ORGANISM: Artificial Sequence
<220> FEATURE:
<223> OTHER INFORMATION: Primer

```
<400> SEQUENCE: 5
ctcggatcca tgcgttactt tgctattgc                                    29

<210> SEQ ID NO 6
<211> LENGTH: 42
<212> TYPE: DNA
<213> ORGANISM: Artificial Sequence
<220> FEATURE:
<223> OTHER INFORMATION: Primer

<400> SEQUENCE: 6
cacggatcct taaaaagcaa aacgttccaa cttgagcaat cc                     42

<210> SEQ ID NO 7
<211> LENGTH: 24
<212> TYPE: DNA
<213> ORGANISM: Artificial Sequence
<220> FEATURE:
<223> OTHER INFORMATION: Primer

<400> SEQUENCE: 7
tttgtcttgg ctcccaaaaa gcca                                         24

<210> SEQ ID NO 8
<211> LENGTH: 33
<212> TYPE: DNA
<213> ORGANISM: Artificial Sequence
<220> FEATURE:
<223> OTHER INFORMATION: Primer

<400> SEQUENCE: 8
ttaaaaagca aaacgttcca acttgagcaa tcc                               33

<210> SEQ ID NO 9
<211> LENGTH: 29
<212> TYPE: DNA
<213> ORGANISM: Artificial Sequence
<220> FEATURE:
<223> OTHER INFORMATION: Primer

<400> SEQUENCE: 9
ctcggatcca tgcgttactt tgctattgc                                    29

<210> SEQ ID NO 10
<211> LENGTH: 60
<212> TYPE: DNA
<213> ORGANISM: Artificial Sequence
<220> FEATURE:
<223> OTHER INFORMATION: Primer

<400> SEQUENCE: 10
cacggatcct taatgatgat gatgatgatg aaaagcaaaa cgttccaact tgagcaatcc  60
```